United States Patent
Christensen et al.

(10) Patent No.: US 8,764,716 B2
(45) Date of Patent: Jul. 1, 2014

(54) KIT FOR COLLECTING STOOL

(75) Inventors: Claus Bo Voege Christensen, Snekkersten (DK); Peter Kragh, Tikob (DK); Anders Bach, Copenhagen S (DK); Michael Hansen, Strand Esb. (DK); Esben Stroebeck, Hoersholm (DK)

(73) Assignee: Coloplast A/S, Humlebaek (DK)

( * ) Notice: Subject to any disclaimer, the term of this patent is extended or adjusted under 35 U.S.C. 154(b) by 680 days.

(21) Appl. No.: 12/227,480

(22) PCT Filed: May 22, 2007

(86) PCT No.: PCT/DK2007/000242
§ 371 (c)(1),
(2), (4) Date: Nov. 19, 2008

(87) PCT Pub. No.: WO2007/134608
PCT Pub. Date: Nov. 29, 2007

(65) Prior Publication Data
US 2009/0163883 A1 Jun. 25, 2009

(30) Foreign Application Priority Data
May 24, 2006 (DK) .................. 2006 00713

(51) Int. Cl.
*A61F 5/44* (2006.01)
(52) U.S. Cl.
USPC ........... 604/328; 604/326; 604/327; 604/331; 604/332; 604/333; 604/334; 604/335; 604/336; 604/337; 604/338; 604/339; 604/340; 604/341; 604/342; 604/343; 604/344

(58) Field of Classification Search
USPC ......... 604/328, 326, 327, 331, 332, 333, 335, 604/336, 337, 338, 339, 341, 342, 343, 344, 604/334, 340
See application file for complete search history.

(56) References Cited

U.S. PATENT DOCUMENTS 4,300,560 A 11/1981 Steer et al.
4,445,898 A 5/1984 Jensen
(Continued)

FOREIGN PATENT DOCUMENTS

EP 0117016 8/1984
EP 0213721 3/1987
(Continued)

OTHER PUBLICATIONS

"Nursing Care of the General Pediatric Surgical Patient" (Barbara Vollenhover Wise, 2000; p. 275);link to page: http://books.google.com/books?id=n3JJO2FfL80C&Ipg=PA275&ots=FIVvy23UWM&dq=Stoma%20size%20(Barbara%20Vollenhover%20Wise%2C%202000).&pg=PA275#v=onepage&q&f=false.*

Primary Examiner — Tatyana Zalukaeva
Assistant Examiner — Ginger T Chapman
(74) Attorney, Agent, or Firm — Coloplast Corp., Coloplast A/S; Nick Baumann

(57) ABSTRACT

A kit for collecting stool, comprising an adapter (1) for connecting the anus or a perianal stoma of a user to a peripheral device, said adapter comprises a flexible adhesive plate (2) having first through going hole, a flexible tube (3) extending from a first opening (11) to a second opening (12) and a first flexible coupling plate (4) having a second through going hole, wherein the flexible tube is attached to the flexible adhesive plate in an area surrounding the first opening and the flexible tube is attached to the first flexible coupling plate in an area encircling the second opening, allowing fluid communication from the first through going hole to the second through going hole through the flexible tube, and a peripheral device (20, 60) for coupling to the adapter.

16 Claims, 5 Drawing Sheets

(56) References Cited

U.S. PATENT DOCUMENTS

| | | | |
|---|---|---|---|
| 4,468,227 A * | 8/1984 | Jensen | 604/327 |
| 4,553,967 A * | 11/1985 | Ferguson et al. | 604/317 |
| 4,604,095 A | 8/1986 | Samuelsen | |
| 4,784,656 A * | 11/1988 | Christian | 604/355 |
| 4,973,323 A | 11/1990 | Kaczmarek et al. | |
| 5,423,782 A * | 6/1995 | Wolrich | 604/339 |
| 5,429,626 A | 7/1995 | Fenton | |
| 5,911,786 A * | 6/1999 | Nielsen et al. | 73/427 |
| 7,976,522 B2 * | 7/2011 | Hansen et al. | 604/338 |
| 2005/0027266 A1* | 2/2005 | Howlett | 604/317 |
| 2006/0189957 A1* | 8/2006 | Howlett | 604/403 |
| 2007/0255240 A1* | 11/2007 | Ciok | 604/339 |
| 2008/0269698 A1* | 10/2008 | Alexander et al. | 604/332 |

FOREIGN PATENT DOCUMENTS

| | | | | |
|---|---|---|---|---|
| EP | 0272816 | 6/1988 | | |
| EP | 0463359 | 1/1992 | | |
| EP | 0981311 | 11/1998 | | |
| EP | 1018325 | 7/2000 | | |
| EP | 1348412 | 10/2003 | | |
| GB | 2058011 | 2/1981 | | |
| GB | 2115288 | 9/1983 | | |
| GB | 2193439 | 2/1988 | | |
| GB | 2351238 A * | 12/2000 | | A61F 5/443 |
| JP | 58165843 | 9/1983 | | |
| JP | 2002534158 | 10/2002 | | |
| JP | 2003010220 | 1/2003 | | |
| JP | 2003305072 | 10/2003 | | |
| WO | 2004/105657 | 12/2004 | | |

* cited by examiner

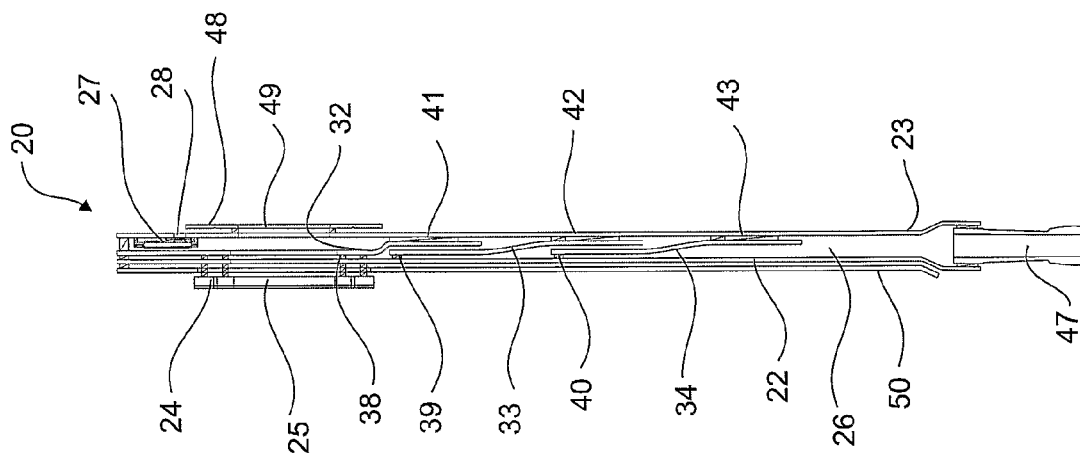
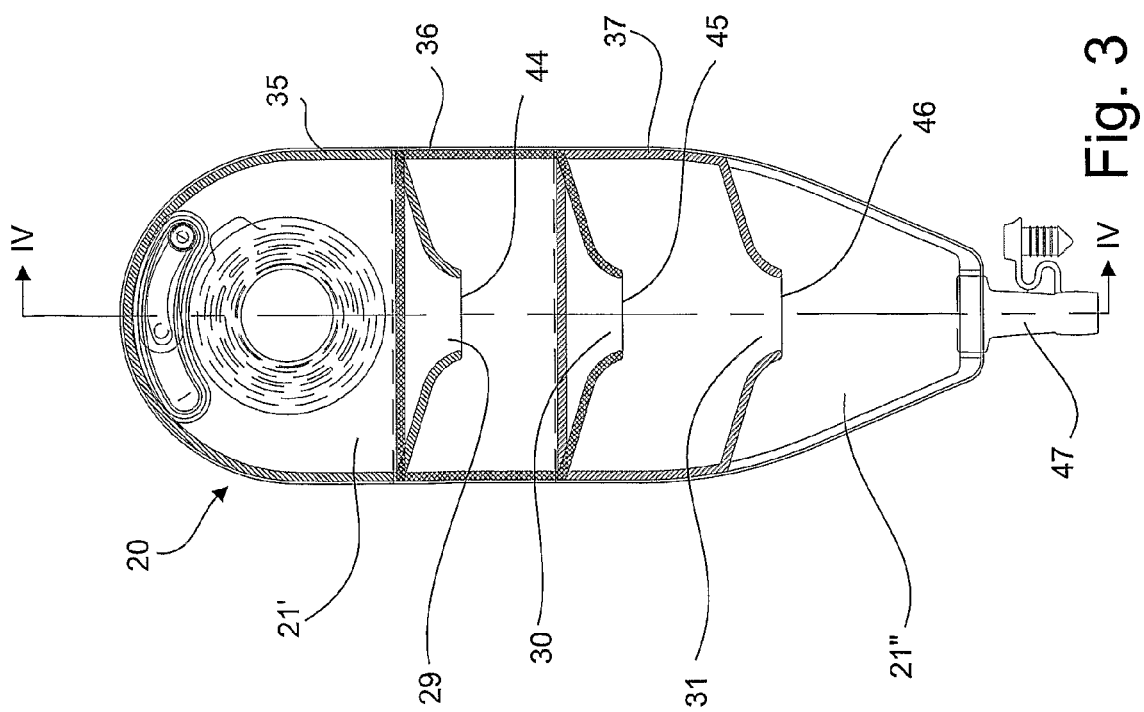

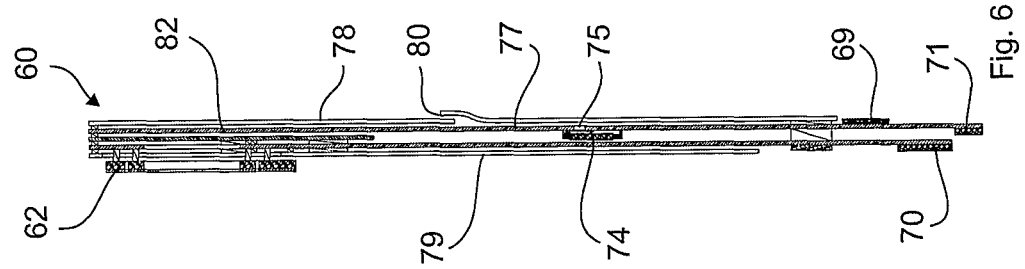
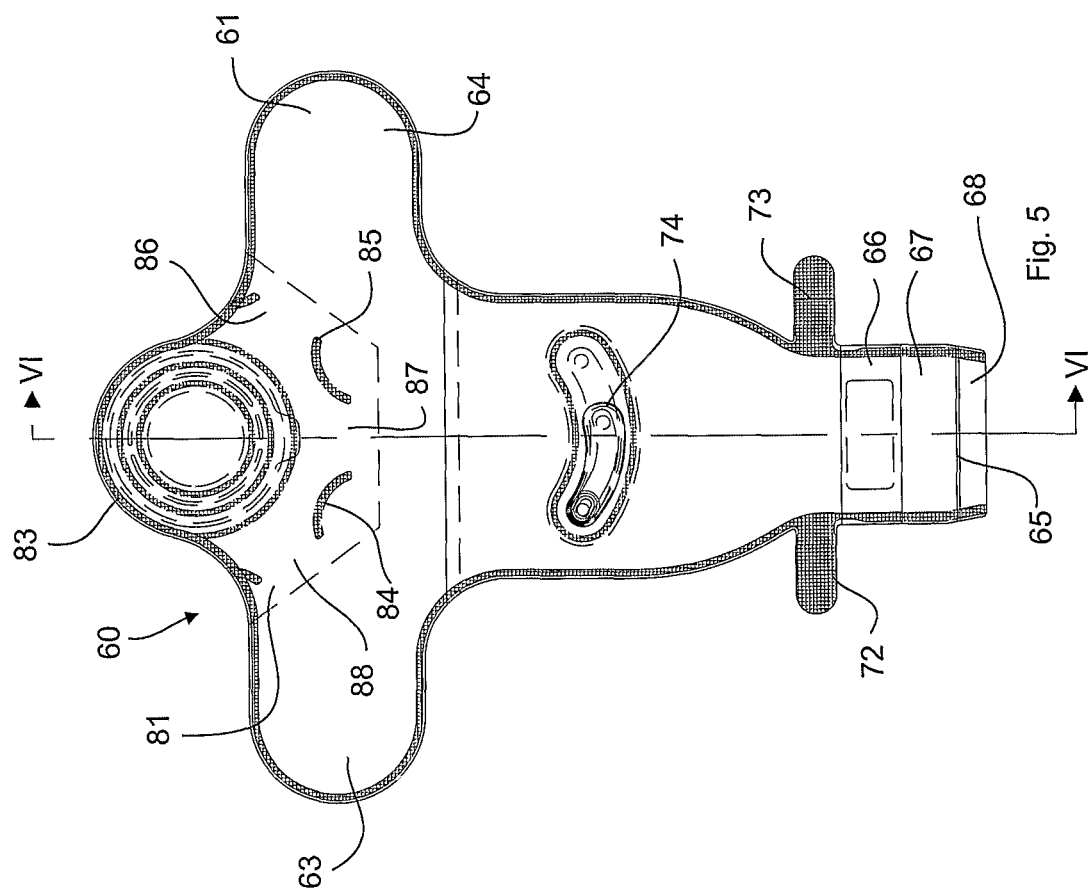

KIT FOR COLLECTING STOOL

This is a national stage of PCT/DK2007/000242 filed May 22, 2007 and published in English, which has a priority of Denmark No. PA200600713 filed May 24, 2006, hereby incorporated by reference.

FIELD OF THE INVENTION

The present invention relates to an adapter connecting the anus or perianal stomas to a peripheral device, such as a bag for collecting stool; a peripheral device, which is connectable to an adapter connecting the peripheral device to the anus providing a liquid tight fit; and a kit comprising an adapter and a peripheral device.

BACKGROUND OF THE INVENTION

Faecal incontinence is a common problem among for example paralysed persons, e.g. paraplegics or tetraplegics or patients in coma. Furthermore, bedridden persons are typically not themselves capable of going to the toilet on their own and it is not always that someone is around to aid them. Thus there is a need for collecting stool from such persons, preventing that it is leaked into the surroundings. Especially in cases where persons suffering from diarrhea and are in a coma it is of interest to be able to collect their stool as it typically is very frequent and the nursing personal will not be alerted of any discomfort to the person.

Different solutions for collecting such stool has been attempted to meet this need, which has resulted in different devices.

One such device is the Drainable Fecal Collector produced by Hollister. This is a bag, which is adhered around anus allowing stool to be received herein.

However, such bags have to be changed frequently which results in a high risk of skin irritation where the bag is adhered. Thus, there furthermore exists a need for preventing such frequent change of bags while still being able to collect stool. Furthermore, many bags described in the prior art suffer from a bad fit around the anus, which often result in leaks.

U.S. Pat. No. 4,784,656 discloses a fecal incontinence receptacle comprising generally a gasket for sealingly engaging an area substantially adjacent to a stoma or anus of a wearer to form a liquid-tight seal there between, a conduit joined to the gasket for providing a passageway for discharge received from the stoma or anus of the wearer to pass there through, and a disposable receptacle detachably connected to the conduit for collecting and disposing of fecal matter received from the conduit.

However, as the patient is often bedridden or confined to e.g. a wheel chair the patient will often sit or lie on parts of the device. Hard device and parts of such devices will have a tendency to create discomfort for the patient and may even cause ulcers and other types of sores.

SUMMARY OF THE INVENTION

In one aspect the invention discloses an adapter for connecting the anus or a perianal stoma of a user to a peripheral device, said adapter comprises a flexible adhesive plate having a first through going hole, a flexible tube extending from a first opening to a second opening and a flexible coupling flange having a second through going hole, wherein the flexible tube is attached to the flexible adhesive plate in an area encircling the first opening and the flexible tube is attached to the flexible coupling flange in an area surrounding the second opening, allowing fluid communication from the first through going hole to the second through going hole through the flexible tube.

This provides an adapter, which allows for a flexible coupling between the adapter and the peripheral device when the flexible coupling flange of the adapter is coupled with a flexible coupling plate of the peripheral device. This has the advantage that when in use the flexible coupling will follow the contour of the body when pressure is applied providing a coupling which is more comfortable for the user and which also reduces the risk of creating ulcers for bedridden users who may have to lie on parts of or the whole adapter, peripheral device and/or the coupling there between.

In the following the term flexible should be read in relation to the human body. The flexible adhesive plate is capable of adapting to the shape around the anus and follow movements in that area while still providing a liquid tight seal between the area around the anus or the perianal stoma and the flexible adhesive plate, and between the peripheral device and the flexible coupling flange. The flexible tube is capable of expanding to allow stool to pass from the anus to the peripheral device and of collapsing when the buttocks are flexed or moved. The flexible coupling flange is flexible so as to follow the contour of the body when the user sits or lies down or any outside force is applied. Thus, the different flexible parts of the adapter conform to the shape of the body in different situations.

In general such flexible materials are known to the person skilled in the art and thus from having been presented the invention as disclosed herein the person skilled in the art will be capable of choosing such flexible materials. For example the flexible adhesive plate can be formed of a hydrocolloid adhesive formed on a polyethylene-backing layer. Such construction is for example known from adhesive ostomy devices. The flexible tube may for example be formed of a polymer foil. The flexible coupling flange may for example be formed of a polyethylene flange with a thickness between 0.5-3 millimeters. Such coupling flanges are for example also known from adhesive coupling arrangements within ostomy devices.

It should be understood that since the adapter is for connecting the anus or a perianal stoma of a user to a peripheral device, specific demands and criteria would have to be fulfilled. Such demands will typically be that the materials used in the adapter are of medical grade and thus accepted to be placed in contact with the human body over longer periods of time.

The through going holes will typically be oval in shape; however, the holes may be formed with many other shapes, for example circular or triangular.

The flexible tube may be attached to the flexible adhesive plate and the flexible coupling flange in many different ways. This may for example be done by gluing or welding the components together in a fluid tight manner.

Furthermore, the flexible tube may be formed in many different ways depending on material, production technique etc. In one simple embodiment the tube is a hollow cylinder formed of a polymer, in another embodiment it can be formed as a hollow cylinder having a tapering surface, i.e. having a conical shaped surface, and in yet another embodiment the tube may be formed two conical shaped hollow cylinders which are welded together. It should be understood that the function of the tube in the present invention primarily is to provide a canal for fluid communication between the first opening and the second opening and as a spacer for separating the flexible adhesive plate and the flexible coupling flange.

In one embodiment of an adapter according to the invention the length of the tube varies along the perimeter of the tube. This has the effect that when flexible adhesive plate is adhered around the anus and a pull is exerted on the first flexible coupling the pulling force will be directed to the flexible adhesive plate through the shortest length of the tube. Thus by orienting the adhesive plate and the flexible tube the pulling force may advantageously be directed to areas of the flexible adhesive plate, which are adhered to skin areas less sensitive to pulling forces. It should be noted that in the context herein the pulling force is a force applied in a direction away from the body when the adapter is adhered thereto, typically the pulling force may also be understood as being directed from the flexible adhesive plate towards the flexible coupling flange.

It should be understood that when referring to a length of the tube it is the length between the adhesive plate and the coupling flange along the surface of the tube. Thus the same tube being in a respectively collapsed position and in an outstretched position will still have the same length in both positions.

It should be understood that the perimeter of the tube typically would correspond to the circumference of the tube, whether the tube has a circular, square or other cross sectional shape.

The pulling force will not always be directed perpendicular from the flexible adhesive plate, or perpendicular to the flexible coupling flange. Thus, in order to allow some tolerance in the direction of the pulling force and avoid that a pull is distributed to undesirable areas of the skin the difference between the maximal length and the minimal length may in one embodiment be at least five millimeters, preferably at least ten centimeters.

In one embodiment of an adapter 1 according to the invention (See FIG. 1) the first through going hole 5 is eccentrically arranged in the adhesive plate 2, defining a first distance L1 and a second distance L2 of the adhesive plate 2 extending along opposite sides of the first through going hole 5. This has the effect that the extent from the center C of the through going hole 5 to the periphery of the adhesive plate 2 will have varying distances (e.g., L1 and L2 as shown in FIG. 1) around the adhesive plate 2 and thereby create areas A1 with larger adhesive surfaces than others, for example area A2 (e.g., area A1 associated with longer distance L1 is greater the area A2 associated with the shorter distance L2).

The larger adhesive areas may advantageously be provided in this way for different reasons. For example some skin surfaces around the anus are larger than others and are thus capable of receiving larger adhesive areas, moreover, larger adhesive areas will distribute forces over a larger skin area and thereby it may be possible to distribute undesirable high pulling forces in specific areas.

Furthermore, adhesive areas having a smaller area are provided in order to fit the flexible adhesive plate tightly around the anus providing a fluid tight seal.

In a preferred embodiment of an adapter according to the invention a symmetry axis of the adhesive plate is in the plane of the adhesive plate and the symmetry axis intersects the centre axis of the first through going hole. This provides an adhesive plate with corresponding adhesive areas on opposite sides of the symmetry axis having corresponding adhesive properties.

Furthermore, the perineum of the intergluteal area of female humans typically have a distance between 1.7-3 centimeters and male humans have a corresponding distance between the anus and scrotum of 3-7 centimeters. Thus in one embodiment of an adapter according to the invention the first distance is between 1.7 and 3 centimeters and in another embodiment the first distance is between 3 and 7 centimeters.

Furthermore, for children and babies this distance is even smaller, typically 0.5-1.7 centimeters.

However, on the sacral part of the intergluteal area there is a larger skin area suitable for adhering the adhesive plate. Thus in one embodiment of an adapter according to the invention the second distance is at least two times the first distance.

When applied around the anus the flexible adhesive plate will have to be capable of being bent into many different shapes as the user moves around and in order to adapt to different physiologies. In many situations the flexible adhesive will even be bent back almost 180 degrees, whereby the backing of the flexible adhesive plate (i.e. the side not adhering to the skin) will be bent onto itself. In this situation it is preferred that the flexible adhesive plate does not get into contact with against the flexible coupling flange or the peripheral device as there might be a risk that this might uncouple the peripheral device from the adapter and thereby stool might spill out into the surroundings.

Thus, in order to reduce this risk the length of the tube may advantageously be longer than any distance perpendicular to and from the centre axis of the first through going hole to any point on the periphery of the flexible adhesive plate.

Typically the adhesive plate is folded around its symmetry axis. Thus, the length of the tube may advantageously be longer than the longest distance from the symmetry axis to any point on the periphery of the flexible adhesive plate.

In a another aspect the invention discloses a peripheral device for coupling to the adapter as described, the peripheral device comprising at least one flexible coupling plate for adhesively coupling with the flexible coupling flange of the adapter, and a third through going hole arranged in the at least one flexible coupling plate.

This provides a peripheral device that is easy to couple with the adapter as described herein and when coupled provides a flexible coupling which easily will conform to the shape of the body. Typically this flexible coupling is provided by the flexible coupling flange and the flexible coupling plate, wherein the flexible coupling plate comprises an adhesive which adheres to the flexible coupling flange in a fluid tight flexible coupling.

Furthermore, different peripheral devices may be used while the adapter is placed around the anus preventing irritation of the skin caused by replacement of different peripheral devices.

It should be understood that the same consideration to the choice of flexible materials and materials suitable in use with the human body should be taken with respect to peripheral device as with the adapter as described previously. For example the flexible coupling plate may be formed of a hydrocolloid adhesive or an acrylic adhesive in order to releasable adhere to the flexible coupling flange on the adapter.

Many different types of peripheral devices may be coupled to the adapter, each serving different purposes. In the following different types of features suitable for implementing in such a peripheral device will be described. The features may be implemented separately in separate peripheral devices or in a number of different combinations providing peripheral devices for many different purposes.

Furthermore, although the peripheral device as described herein is adapted to be capable of coupling to an adapter also as described herein, i.e. providing a flexible coupling, it should be understood that applying the same features to peripheral devices having different coupling arrangements with an adapter is also within the teachings of this document.

One typical function of the adapter and thereto coupled peripheral device is to collect stool from the anus, thus in one embodiment according to the invention the peripheral device comprises a flexible bag wherein the flexible coupling plate is arranged in a first half of the bag. This allows for stool to be contained in the bag, which when full may be uncoupled from the adapter and disposed. A new bag subsequently be coupled to the adapter if need be.

In one embodiment of a peripheral device according to the invention a drainage port is arranged in a second half of the bag. Thus, the peripheral device may be easily emptied when the bag is full.

In order to prevent stool to run back into the adapter and risk causing clogging or irritation of exposed skin around the anus at least one non-return valve may arranged between the flexible coupling plate and at least one section of the bag allowing fluid to run downstream from the flexible coupling plate to the at least one section of the bag, but preventing fluid to run upstream.

In one embodiment which is simple to produce and very reliable the at least one non-return valve comprises a flexible wall extending between a first side of the bag to an opposite second side of the bag, wherein an upstream end of the flexible wall is fixed to the first side of the bag in a fluid tight manner along the full extent of the first side of the bag in a direction transverse to the stream, and wherein an downstream end of the flexible wall is partly fixed to the second side of the bag in a fluid tight manner along the extent of the second side of the bag in a direction transverse to the stream.

In yet another embodiment of a peripheral device according to the invention a filter is provided in the peripheral device allowing gas to escape from the device. Such a filter serves primarily to prevent that the bag is blown up by gas creating discomfort for the user and may also compromise the attachment of both the adapter and the peripheral device due to pressure building up inside. Furthermore, such filters may also be provided in order to remove obnoxious smells from the exiting gasses/flatulence.

Having understood the present invention a person skilled in the art will be able to use many different types of filter arrangement known within the art. For example filters known from ostomy appliances may be use, such as the filter arrangement described in EP 0981311.

In some occasions it may be of interested to monitor the area around the anus. This may be due to suspicion of skin irritation in that area or in order to monitor the stool coming there from. For such monitoring purposes the peripheral device may advantageously comprise a transparent section arranged opposite the flexible coupling plate.

In other situations it may be of interest to insert an instrument into the periphery device, the adapter or/and the anus. This may for example be a thermometer or a instrument for taking a sample of the stool. Thus, the peripheral device may comprise an access port allowing entry into the peripheral device.

In one embodiment the peripheral device further comprises an absorber cap capable of absorbing a fluid. Such an absorber cap may be provided in a bag, such as the bag described previously, in order to absorb some of the liquid from very fluent stool.

In another embodiment such an absorber cap covers the third through going hole in the flexible coupling plate. This allows for a compact peripheral device which may allows for some movement without the user being annoyed by larger peripheral devices as the absorber cap will absorb stool.

It should be understood that many other types of combinations and modification of a peripheral device might be provided within the scope of the invention. Thus in one simple embodiment the flexible coupling plate is simply covered with a cap which prevents fluid to exit the through going hole of the flexible coupling plate.

Although the adapter and the periphery device are described as two separate units above, they are both dependent on each other in order to operate properly. Thus, in another aspect the invention discloses a kit for faecal management comprising an adapter as described previously and at least one peripheral device as described previously.

BRIEF DESCRIPTION OF THE DRAWINGS

The invention is disclosed more in detail with reference to the drawings in which FIG. 3 shows one embodiment of a peripheral device according to the invention, FIG. 4 shows the above in section along line IV-IV in FIG. 3, FIG. 5 shows another embodiment of a peripheral device according to the invention, FIG. 6 shows the above in section along line VI-VI in FIG. 5.

DETAILED DESCRIPTION OF THE PRESENT INVENTION

Figure 1:
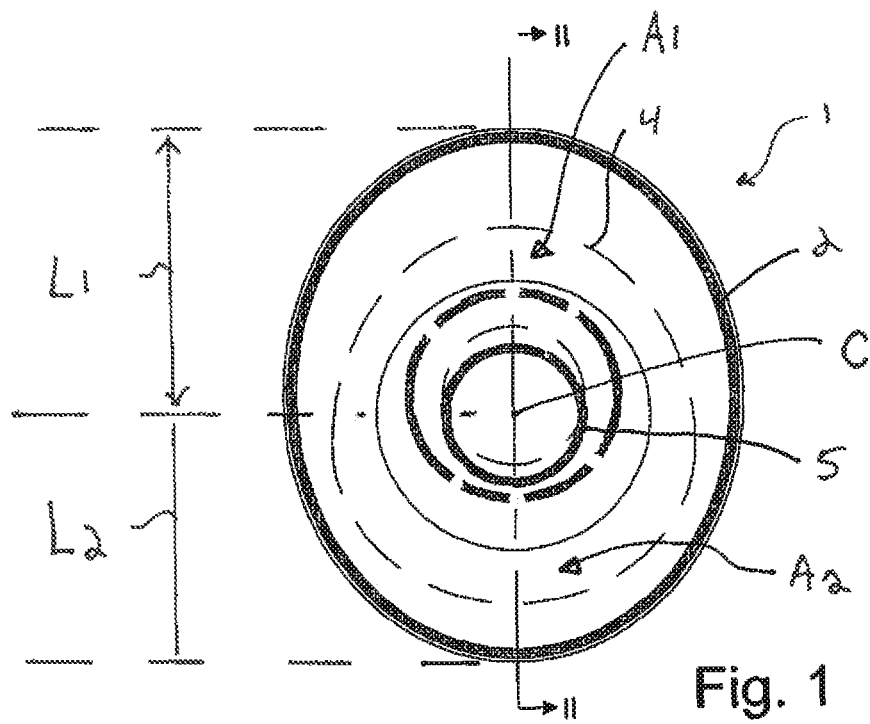
FIG. 1 shows an adapter according to the invention.
Figure 2:
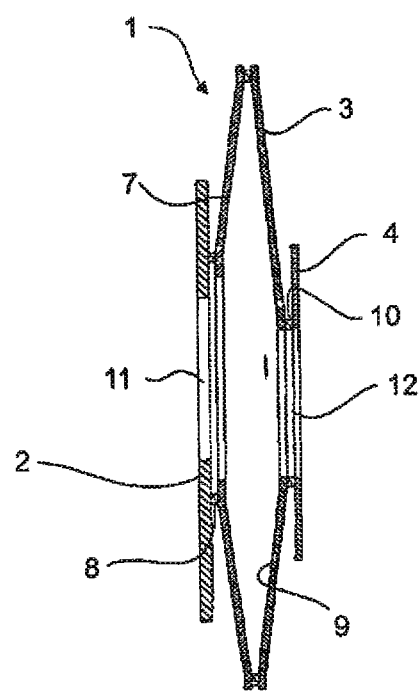
FIG. 2 shows the adapter in section along line II-II in FIG. 1.

FIGS. 1 and 2 shows an adapter 1 for connecting the anus or a perianal stoma of a user to a peripheral device (not shown) providing a liquid tight seal.

The adapter is formed of a flexible adhesive plate 2 formed of an hydrocolloid adhesive arranged on a polymer backing layer, a flexible tube 3 formed of a polymer film, e.g. a so-called barrier foil being impermeable to moisture and smell, and a flexible coupling flange 4 formed of a polymer.

A first through going hole 11 is formed in the flexible adhesive plate 2 and a second through going hole 12 is formed in the flexible coupling flange 4.

A first end 7 of the tube is attached to the flexible adhesive plate around the first through going hole by a first weld 8, and a second end 9 of the tube is attached to the flexible coupling flange around the second through going hole by a second weld 10.

Thus fluid passage is possible through the first through going hole, into the tube through a first opening 11 defined by the first end of the tube; out of the tube through a second opening 12 defined by the second end of the tube; and out through the second through going hole.

When used the flexible adhesive plate is adhered around the anus, allowing passage of stool through the first through going hole.

The adapter is shown in its collapsed state in FIGS. 1 and 2. However when extended the length between the flexible adhesive plate and the flexible coupling flange extends beyond the gluteals when the flexible adhesive plate is attached around the anus. In other words the flexible tube function as a spacer between the flexible adhesive plate and the flexible coupling flange, allowing the flexible coupling flange to be placed in a distance away from the human body.

FIGS. 3 and 4 shows a first embodiment of a peripheral device 20 according to the invention, which can be adhered to the flexible coupling flange of e.g. the adapter shown in and described with reference to FIGS. 1 and 2.

The peripheral device 20 is formed of a bag 21 made of a thin polymer film. The bag is formed by welding a first polymer sheet 22 and a second polymer sheet 23 together along their edges. On one half 21' of the bag there is provided a flexible coupling plate 24, wherein a through going hole 25 is provided which provides access to the compartment 26 of the bag. The coupling plate is formed of a hydrocolloid adhesive provided on a backing layer of polyurethane.

Thus the peripheral device 20 will collect stool from an adapter when the adhesive plate of the adapter is adhered around the anus. The peripheral device 20 is typically adhered to an adapter by aligning the though going hole of the flexible coupling flange with the through going hole of the flexible coupling plate and pressing the two together.

The bag of the peripheral device is further provided with a gas filter 27, which provides communication with the outside of the bag through the hole 28. This allows for example flatulence to escape, so that the bag does not get bloated and uncomfortable to wear. Such filters are generally known from e.g. ostomy devices and are formed to prevent that only gas escapes and not liquid. Furthermore, many such filters may have incorporated deodorizers, which neutralises the smell of escaped gasses. However, when the skilled person has acknowledged that such filters may be used herein many different types of gas filters may be used which are known within the art.

Within the bag there is furthermore provided three non-return valves 29, 30 and 31. To prevent stool contained in the bag to flow back through the through going hole of the flexible coupling plate and into the adapter.

The non-return valves are each formed of a polymer film wall 32, 33 and 34, which is attached inside the bag by a weld 35, 36 and 37 respectively. Each weld has a first weld section 38, 39 and 40 and a second weld section 41, 42 and 43, wherein the first weld section attaches the respective wall to the first polymer sheet 22 and the second weld section attaches the respective wall to the second polymer sheet 23.

Furthermore, when looking at the weld section relative to the stream, i.e. the stream is the direction the stool will flow from the flexible coupling plate arranged on the first half 21' of the bag 21 towards a second half 21" of the bag, the first weld section is arranged upstream and the second weld section is provided downstream. The second weld section is furthermore interrupted in at least one area providing openings 44, 45 and 46.

Thus when stool flows in a downstream direction the polymer film walls, the second polymer sheet and the second weld section will function as funnels allowing the stool to flow through the openings 44, 45 and 46 in the second weld section. However, in case the stool already collected in bag starts to flow upstream the polymer film walls will collapse against the surface of the second polymer sheet, thereby preventing the stool to flow through the opening.

In the second half of the bag 21 there is provided a drainage port 47. The drainage allows for thin stool to be emptied easily, whereby the peripheral device 20 may be worn for an extended period of time. Furthermore the drainage port may also be used as an extra outlet for gasses in case of excessive flatulence, which might overload the filter 27.

Opposite the flexible coupling plate, which is arranged in the first polymer sheet 22, there is arranged a second flexible coupling flange 48 in the second polymer sheet 23. This second flexible coupling flange allows for additional peripheral devices to be attached. If no additional peripheral devices are attached a cover (not shown) is adhered in order to close of the through going hole 49 in the second flexible coupling flange.

When attached to the adapter the peripheral device will typically abut against the skin of a user. In order to provide increased comfort for the user a non-woven sheet 50 covers the first polymer sheet 22 on the side of the peripheral device that faces the skin when the peripheral device is used. Other types than non-woven materials may be used as long as they are suitable to abut against human skin for longer periods of time.

FIGS. 5 and 6 shows a second embodiment of a peripheral device 60 where a different shaped bag 61 extends from a flexible coupling plate 62. The bag is ergonomically shaped with two flaps 63, 64 extending transversely to the direction of the stream, which is the direction from the flexible coupling plate towards the outlet 65. The flaps will extend under the buttocks and conform to the shape of the body making the bag more comfortable to wear compared to many other known bags for collecting stool.

The outlet 65 is formed as three section 66, 67 and 68 provided with three stiffeners 69, 70 and 71 respectively, which allows the outlet to be easily closed by folding the three sections together and locking them in position by the two Velcro flaps 72 and 73.

The bag is furthermore provided with a gas filter 74, which through opening 75 in the bag allows gasses such as flatulence to escape and thereby preventing that the bag inflates and becomes uncomfortable to wear or even prevent that the bag detaches due to excess pressure.

Two non-woven sheet 78,79 covers the sides of the bag, which is formed of two transparent polymer sheets 76,77 which are welded together. In the non-woven sheet 78 on the side opposite the flexible coupling part there is provided a slit 80, which allows for visual inspection of the content of the bag through the transparent polymer sheet 77 underneath.

In order to prevent backflow through the flexible coupling plate 62 a non-return valve 81 is provided within the bag. The non-return valve is formed of a polymer film wall 82. The polymer film wall is by three welds 83, 84 and 85 attached to the same polymer sheet 76 to which the flexible coupling plate is connected. The three welds are interrupted by three openings 86, 87 and 88. Thus a funnel like non-return valve as the one described in the first embodiment of the peripheral device above is provided.

Figure 7:
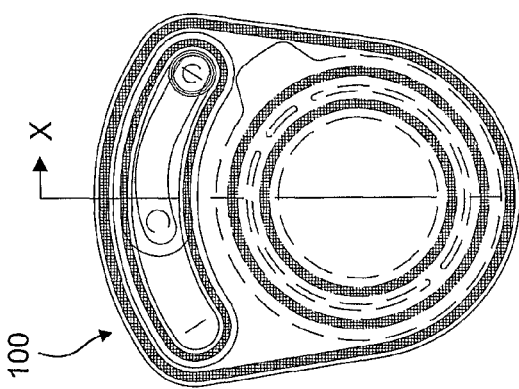
FIG. 7 shows another embodiment of a peripheral device according to the invention.
Figure 8:
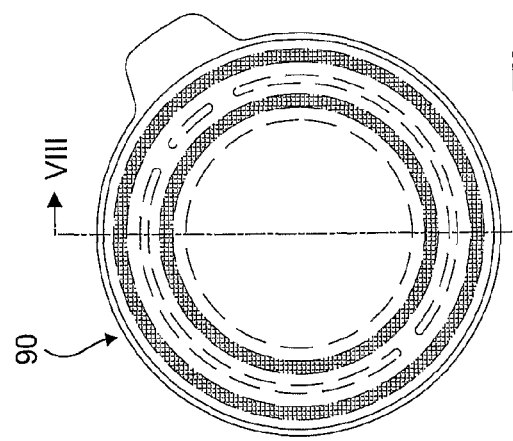
FIG. 8 shows the above in section along line VIII-VIII in FIG. 7.

In another embodiment of the peripheral device, as shown in FIGS. 7 and 8, the peripheral device is a cap 90 for closing of the through going hole (reference number 49 in FIG. 4, and 12 in FIG. 2) in the flexible coupling flange (reference number 48 in FIG. 4 and 4 in FIG. 2).

The cap is formed of a flexible coupling plate 91 formed of an adhesive hydrocolloid disposed on a polyurethane backing layer which is welded to a polymer cover sheet 92, which covers the through going hole in the flexible coupling plate 93.

Figure 9:
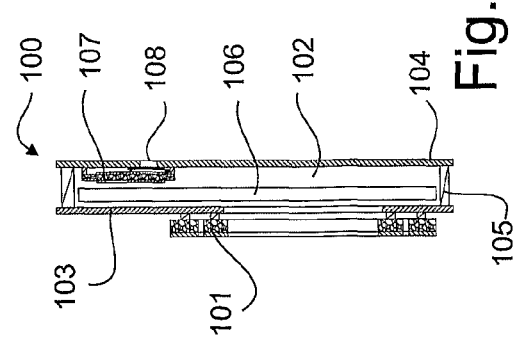
FIG. 9 shows another embodiment of a peripheral device according to the invention.
Figure 10:
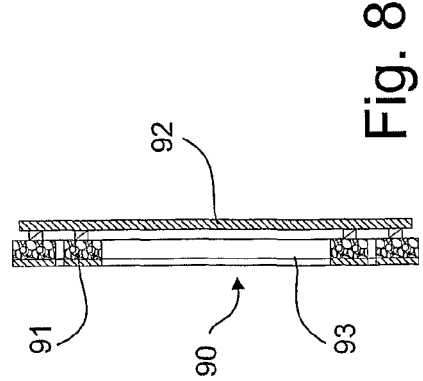
FIG. 10 shows the above in section along line X-X in FIG. 9.

FIGS. 9 and 10 shows a second embodiment 100 of a cap for connecting to the flexible adhesive flange the cap allows for gasses, such as flatulence, to escape.

The cap 100 is formed of a flexible coupling plate 101 formed of an adhesive hydrocolloid disposed on a polyurethane backing layer that is welded to a compartment 102. The compartment is defined by two polymer sidewalls 103 and 104 and an encircling polymer wall 105 attached to the periphery of the respective sidewalls.

In the compartment there is provided an absorber 106 for absorbing liquid and a gas filter 107 which communicates with the outside of the compartments through a hole 108 in one of the polymer sidewalls 104.

Figure 12:
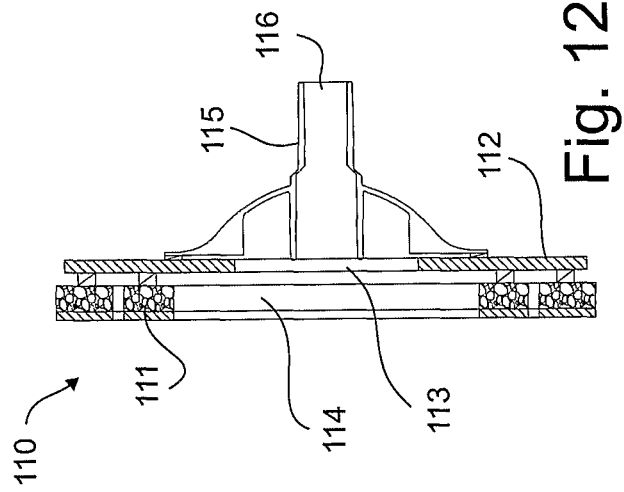
FIG. 12 shows the above in section along line XII-XII in FIG. 11.
Figure 11:
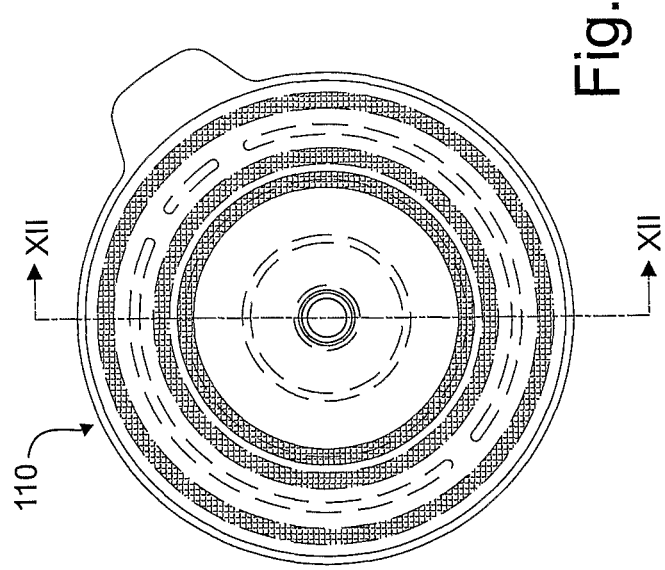
FIG. 11 shows another embodiment of a peripheral device according to the invention.

FIGS. 11 and 12 shows another embodiment of a peripheral device in the form of an interface unit 110. The interface unit is formed of a flexible coupling plate 111 formed of an adhesive hydrocolloid disposed on a polyurethane backing layer. The backing layer is welded to a polymer disc 112 and is provided with a first through going hole 113 that is aligned with, and communicates with a second through going hole 114 of the flexible coupling plate.

An access port 115 covers the first through going hole 113 and is welded to the polymer disc, on the opposite side of the flexible coupling plate. The access port is provided with a canal 116, which communicates with the first and second through going holes.

When in use it is thus possible to access the anus through the canal in the access port. Thus a thermometer may be inserted in order to take the temperature of a user or a sample of the spool may be taken. Many other devices, e.g. for surgery, may also be inserted through the canal.

It should be understood that the above embodiments are examples only, and many other embodiments and combinations of the above described can be imagined within the scope of this invention.

It should further be noted that as it has been described, a flexible coupling is provided when a flexible coupling flange and the flexible coupling plate is coupled together. However, in the above the flexible coupling plate has been provided with an adhesive that adhered the coupling plate to the flexible coupling flange. It is within the scope of the invention that the flexible coupling flange also could have adhesive disposed thereon and/or no adhesive is provided on the flexible coupling plate.

Furthermore, many different materials than those mentioned herein may be used in order to produce the adapter and the peripheral device as long as they are materials suitable for use in contact with the human skin.

EXAMPLE 1

In one embodiment the first flexible coupling plate and the second flexible coupling plate may be provided as corresponding parts in the Easiflex coupling produced by Coloplast A/S. This coupling has previously been used for coupling ostomy base plates, corresponding to the first flexible coupling plate, and ostomy pouches, corresponding to the second flexible coupling plate, together. The Easiflex coupling arrangement is provided as flexible coupling plates, which are adhered together. Compared to mechanical couplings this provides a much more comfortable and capable of following the contour of the body as users, for example bedridden persons, moves around.

In order to understand the advantage hereby a comparative test has been performed wherein the flexural properties of the adhesive coupling (i.e. the first and second flexible coupling plates provided as Easiflex coupling plates) vs. mechanical coupling has been tested to verify the degree of flexibility of the coupling according to the invention.

The couplings are tested by applying the same deflection with respect to their height, and the load force is measured corresponding to the deflection.

The coupling sizes are chosen so they have similar centre hole diameter, where output can be collected through.

The test is a standard test, ASTM D790-96a. This test uses a three-point loading system utilising centre loading on a simply supported beam as test method.

The parameters for the test are as follows:
Support span (L)=40 mm
Radii of rotatable specimen supports=10 mm
Radii of loading nose=5 mm
Rate of cross-head motion (R)=20 mm/min
Deflection=10 mm The test specimens used are
(E) Easiflex 50 mm ostomy coupling plate with ostomy pouch, which is an adhesive coupling produced by Coloplast A/S.
(M) MC2002 50 mm ostomy coupling plate with ostomy pouch, which is a mechanical coupling produced by Coloplast A/S.
(H) 24200 45 mm ostomy coupling plate with ostomy pouch, which is a mechanical coupling produced by Hollister.

| Test specimen | Centre hole diameter of coupling (mm) | Height of test specimens (mm) | Bending force (N) @ 10 mm deflection |
|---|---|---|---|
| E | 48.5 | 2.3 | 4.5 |
| M | 45 | 6.5 | 58 |
| H | 44 | 5.2 | 46.5 |

As can be seen the bending force for the adhesive coupling is a factor ten lower than the mechanical couplings, thus providing a much better flexibility to the coupling allowing it to follow the contour of the body in case the user sit, lies or otherwise applies pressure on it.

Thus, it can be understood that the flexible coupling plates are capable of providing a relative flexible coupling when coupled with a corresponding flexible coupling plate. In one embodiment such flexibility can thus be defined by the bending force at 10 mm deflection for the assembled coupling and in one embodiment the bending force is less than 10N at 10 mm deflection, preferably less than 6N at 10 mm deflection and in particular 4.5 N at 10 mm deflection.

| Reference numerals | |
|---|---|
| 1. | adapter |
| 2. | flexible adhesive |
| 3. | flexible tube |
| 4. | flexible coupling flange |
| 5. | first through going hole |
| 6. | second through going hole |
| 7. | first end |
| 8. | first weld |
| 9. | second end |
| 10. | second weld |
| 11. | first opening |
| 12. | second opening |
| 20. | first embodiment of a peripheral device |
| 21. | bag |
| 21'. | first half of the bag |
| 21". | second half of the bag |
| 22. | first polymer sheet |
| 23. | second polymer sheet |

-continued

| Reference numerals | |
|---|---|
| 24. | flexible coupling plate |
| 25. | through going hole |
| 26. | compartment |
| 27. | gas filter |
| 28. | hole |
| 29. | first non-return valve |
| 30. | second non-return valve |
| 31. | third non-return valves |
| 32. | first polymer film wall |
| 33. | second polymer film wall |
| 34. | third polymer film wall |
| 35. | first weld |
| 36. | second weld |
| 37. | third weld |
| 38. | first weld section of the first weld |
| 39. | first weld section of the second |
| 40. | first weld section of the third weld |
| 41. | second weld section of the first weld |
| 42. | second weld section of the second weld |
| 43. | second weld section of the third weld |
| 44. | first opening |
| 45. | second opening |
| 46. | third opening |
| 47. | drainage port |
| 48. | second flexible coupling flange |
| 49. | through going hole |
| 50. | non-woven sheet |
| 60. | second embodiment of a peripheral device |
| 61. | bag |
| 62. | flexible coupling plate |
| 63. | first flap |
| 64. | second flap |
| 65. | outlet |
| 66. | first section |
| 67. | second section |
| 68. | third section |
| 69. | first stiffener |
| 70. | second stiffener |
| 71. | third stiffener |
| 72. | first Velcro flap |
| 73. | second Velcro flap |
| 74. | gas filter |
| 75. | opening |
| 76. | first transparent polymer sheet |
| 77. | second transparent polymer sheet |
| 78. | first non-woven sheet |
| 79. | second non-woven sheet |
| 80. | slit |
| 81. | non-return valve |
| 82. | polymer film wall |
| 83. | first weld |
| 84. | second weld |
| 85. | third weld |
| 86. | first opening |
| 87. | second opening |
| 88. | third opening |
| 90. | cap |
| 91. | flexible coupling plate |
| 92. | polymer cover sheet |
| 93. | flexible coupling plate |
| 100. | second embodiment of a cap |
| 101. | flexible coupling plate |
| 102. | compartment |
| 103. | first polymer sidewall |
| 104. | second polymer sidewall |
| 105. | encircling polymer wall |
| 106. | absorber |
| 107. | gas filter |
| 108. | hole |
| 110. | interface unit |
| 111. | flexible coupling plate |
| 112. | polymer disc |
| 113. | first through going hole |
| 114. | second through going hole |
| 115. | access port |
| 116. | canal |

The invention claimed is:

1. An adapter configured between an anus or a perianal stoma of a user and a peripheral device, the adapter comprising:
an adhesive plate for securing the adapter to a patient's body, the adhesive plate having a first axis and a second axis perpendicular to and intersecting the first axis, the first axis extending along one of a height and a width of the adhesive plate, a stoma accommodating hole coaxial with the intersection of the first and second axes, and defining a first adhesive zone on a first side of the first axis and a second adhesive zone on a second side of the first axis opposite the first side of the first axis, the first adhesive zone being larger than the second adhesive zone;
a coupling plate having an opening; and
a flexible tube extending between the adhesive plate and the coupling plate, the flexible tube being expandable in length between the first adhesive plate and the coupling plate, the flexible tube defining a first maximum expansion length on the first side of the first axis and a second maximum expansion length on the second side of the first axis, the first maximum expansion length being less than the second maximum expansion length
wherein the first maximum expansion length directs pulling force exerted on the coupling plate to the first adhesive zone.

2. The adapter according to claim 1, wherein a difference between the first and second maximum expansion lengths of the tube is between five millimeters and ten centimeters.

3. The adapter according to claim 1, wherein the stoma accommodating hole is eccentrically arranged in the adhesive plate.

4. The adapter according to claim 1, wherein the first maximum expansion length of the tube is longer than a distance measured from the axes intersection at the stoma accommodating hole to any point on a periphery on the flexible adhesive plate.

5. A peripheral device for coupling to the adapter according to claim 1, the peripheral device comprising a second flexible coupling plate for adhesively coupling with the flexible coupling plate of the adapter, and a third hole arranged in the second flexible coupling plate.

6. The peripheral device according to claim 5, wherein the peripheral device comprises a flexible bag wherein the second flexible coupling plate is arranged in a first half of the bag.

7. The peripheral device according to claim 6, wherein a drainage port is arranged in a second half of the bag.

8. The peripheral device according to claim 6, wherein at least one non-return valve is arranged between the second flexible coupling plate and at least one section of the bag allowing fluid to run downstream from the second flexible coupling plate to the at least one section of the bag, but preventing fluid to run upstream.

9. The peripheral device according to claim 8, wherein the at least one non-return valve comprises a flexible wall extending between a first side of the bag and an opposite second side of the bag, wherein an upstream end of the flexible wall is fixed to the first side of the bag in a fluid tight manner along the full extent of the first side of the bag in a direction transverse to a stool stream and a downstream end of the flexible wall is partly fixed to the second side of the bag in a fluid tight manner along the extent of the second side of the bag in a direction transverse to the stream.

10. The peripheral device according to claim 5, wherein a filter is provided in the peripheral device allowing gas to escape from the device.

11. The peripheral device according to claim 5, wherein the peripheral device comprises a transparent section arranged opposite the second flexible coupling.

12. The peripheral device according to claim 5, wherein the peripheral device comprises an access port allowing entry into the peripheral device.

13. The peripheral device according to claim 5, wherein the peripheral device comprises an absorber cap capable of absorbing a fluid.

14. A kit for fecal management comprising an adapter according to claim 1 and a peripheral device comprising a second flexible coupling plate for adhesively coupling with the flexible coupling plate of the adapter, and a third hole arranged in the second flexible coupling plate.

15. An adapter configured between an anus or a perianal stoma of a user and a peripheral device comprising:
- a flexible adhesive plate having a first hole, the flexible adhesive plate having a first axis and a second axis perpendicular to and intersecting the first axis, the first axis extending along one of a height and a width of the adhesive plate, a stoma accommodating hole coaxial with the intersection of the first and second axes, and defining a first adhesive zone on a first side of the first axis and a second adhesive zone on a second side of the first axis opposite the first side of the first axis, the first adhesive zone being larger than the second adhesive zone;
- a flexible coupling flange having a second hole; and
- a flexible tube extending between first and second ends, the first end of the tube attached to the flexible adhesive plate and the second end of the tube attached to the flexible coupling flange, the flexible tube configured with opposing side walls extending between the first and second ends that are capable of being flexed from each other,
wherein the opposing side walls have differing absolute lengths to direct any pulling force exerted on the flexible coupling flange to the flexible adhesive plate through a shortest wall of the opposing side walls.

16. An adapter configured between an anus or a perianal stoma of a user and a peripheral device comprising:
- an adhesive plate having a first hole, the adhesive plate having a first axis and a second axis perpendicular to and intersecting the first axis, the first axis extending along one of a height and a width of the adhesive plate, a stoma accommodating hole coaxial with the intersection of the first and second axes, and defining a first adhesive zone on a first side of the first axis and a second adhesive zone on a second side of the first axis opposite the first side of the first axis, the first adhesive zone being larger than the second adhesive zone;
- a coupling flange having a second hole; and
- a flexible tube attached between the adhesive plate and the coupling flange, the flexible tube having a wall extending from a first opening to a second opening, the first hole in the flexible adhesive plate communicating with the first opening and the second hole in the flexible coupling flange communicating with the second opening, the tube providing a path for fluid communication between the first opening,
wherein a length of the wall of the flexible tube varies to provide differentiated elongability of the flexible tube between the first opening and the second opening, the differentiated elongability varying about a circumference of the flexible tube.

* * * * *